(12) United States Patent
Diamond (10) Patent No.: US 11,925,752 B1
(45) Date of Patent: Mar. 12, 2024

(54) ASYMMETRIC TEMPERATURE NASAL BREATHING APPARATUSES AND METHODS

(71) Applicant: Paul Diamond, New York, NY (US)

(72) Inventor: Paul Diamond, New York, NY (US)

( * ) Notice: Subject to any disclaimer, the term of this patent is extended or adjusted under 35 U.S.C. 154(b) by 452 days.

(21) Appl. No.: 17/087,601

(22) Filed: Nov. 2, 2020

Related U.S. Application Data (60) Provisional application No. 62/972,058, filed on Feb. 9, 2020, provisional application No. 62/929,892, filed on Nov. 3, 2019.

(51) Int. Cl.
| | | |
|---|---|---|
| *A61M 15/08* | (2006.01) | |
| *A61M 15/00* | (2006.01) | |
| *A61M 16/06* | (2006.01) | |

(52) U.S. Cl.
CPC .......... *A61M 15/08* (2013.01); *A61M 15/002* (2014.02); *A61M 16/0666* (2013.01); *A61M 2205/3368* (2013.01)

(58) Field of Classification Search
CPC .... A61M 16/0666–0677; A61M 16/00; A61M 16/0461; A61M 2205/36; A61M 2205/3368; A61M 2016/0061; A61M 15/08; A61M 15/002
See application file for complete search history.

(56) References Cited

U.S. PATENT DOCUMENTS

| | | | | |
|---|---|---|---|---|
| 2005/0066976 A1* | 3/2005 | Wondka | ............ | A61M 16/0605 128/207.18 |
| 2007/0283958 A1* | 12/2007 | Naghavi | ................ | A61F 5/566 128/204.23 |
| 2009/0159084 A1* | 6/2009 | Sher | .................. | A61M 16/0666 128/205.24 |
| 2011/0253136 A1* | 10/2011 | Sweeney | ............ | A61M 16/161 128/207.18 |
| 2014/0316485 A1* | 10/2014 | Ackermann | ....... | A61N 1/36132 607/53 |
| 2016/0030696 A1* | 2/2016 | Klenner | ............ | A61M 16/0003 128/207.18 |
| 2016/0158476 A1* | 6/2016 | Tatkov | .............. | A61M 16/0688 128/203.22 |

FOREIGN PATENT DOCUMENTS

| | | | | |
|---|---|---|---|---|
| WO | WO-2014186584 A2 * | 11/2014 | ........ | A61M 16/0666 |
| WO | WO-2015033288 A1 * | 3/2015 | ........ | A61M 16/0666 |
| WO | WO-2017187390 A1 * | 11/2017 | ........ | A61M 16/0006 |

OTHER PUBLICATIONS

Becerra et al., Trigeminal Neuropathic Pain Alters Responses in CNS Circuits to Mechanical (Brush) and Thermal (Cold and Heat) Stimuli, Oct. 18, 2006, The Journal of Neuroscience, 26(42): pp. 10646-10657 (Year: 2023).*

Mercante et al., Auricular Neuromodulation: The Emerging Concept beyond the Stimulation of Vagus and Trigeminal Nerves, Jan. 21, 2018, Medicines, 5(10): pp. 1-12 (Year: 2023).*

* cited by examiner

*Primary Examiner* — Kendra D Carter
*Assistant Examiner* — Arielle Wolff (57) ABSTRACT

In one aspect, the disclosure provides apparatuses for and related methods of delivering inhalation airstreams of different temperatures to the nostrils of a subject. Certain embodiments provide apparatuses for and related methods of alternately delivering inhalation airstreams of different temperatures to the respective nostrils of a subject.

17 Claims, 5 Drawing Sheets

ASYMMETRIC TEMPERATURE NASAL BREATHING APPARATUSES AND METHODS

CROSS-REFERENCE TO RELATED APPLICATIONS

This application claims the benefit of U.S. provisional application Ser. No. 62/972,058 filed Feb. 9, 2020 and 62/929,892 filed Nov. 3, 2019, each of which is hereby incorporated by reference in its entirety.

FIELD OF THE INVENTION

The invention relates to the field of therapeutic breathing apparatuses.

BACKGROUND

Various medical devices are available to address respiratory medical issues such as continuous positive airway pressure (CPAP) machines, bi-level positive airway pressure (BiPAP) machines, and ventilators. CPAP is used to treat sleep apnea by providing a continuous positive pressure airstream via mask or nasal pillow during sleep to reduce airway obstruction and apneas. BiPAP is similar to CPAP but provides two different pressures, one or inhalation and one for exhalation, for patients who have difficulty exhaling with CPAP. In addition to treating sleep apnea, BiPAP is also used to treat respiratory issues associated with amyotrophic lateral sclerosis (ALS), Parkinson's disease, and chronic obstructive pulmonary disease (COPD). Ventilators assist breathing in patients who have difficulty breathing, for example, as a result of pneumonia, COPD or other lung diseases, spinal cord injuries, muscle and nerve disorders. Many ventilators provide BiPAP settings as well as volume controls.

Alternate nasal breathing, is a yoga technique that has been reported to affect the para-sympathetic nervous system and electroencephalographic activity.

SUMMARY OF THE DISCLOSURE

In one aspect, what is provided is an apparatus for asymmetric temperature nostril breathing that includes:
 a first air source of air having a first temperature;
 a second air source of air having a second temperature, wherein the first temperature and the second temperature are different;
 a first air conduit including a first air outlet, said first air conduit configured to deliver air from the first air source to the first air outlet; and
 a second air conduit including a second air outlet, said second air conduit configured to deliver air from the second air source to the second air outlet,
wherein the apparatus is configured to simultaneously deliver air from the first air conduit to the first air outlet and air from the second air source to the second air outlet.

In another aspect, what is provided is an apparatus for asymmetric temperature nostril breathing that includes:
 an air heating element;
 an air cooling element;
 a first air conduit having an air inlet and in fluid communication with a first air outlet, configured to deliver air heated by the air heating element therethrough; and
 a second air conduit having an air inlet and in fluid communication with a second air outlet, configured to deliver air cooled by the air cooling element therethrough,
wherein the apparatus is configured to simultaneously deliver air heated by the air heating element through the first air conduit and air cooled by the air cooling element through the second air conduit.

In still another aspect, what is provided is an alternate nasal breathing apparatus that includes:
 at least one air intake;
 a first air outlet and a second air outlet, wherein the first and second air outlets are sized, configured and mutually disposed for respective at least substantially sealable insertion into a first nostril and a second nostril of a human user; and
 one or more actuatable valves operable to switch between
  a first state (flowpath configuration) in which the at least one air intake is in fluid communication with the first air outlet and not the second air outlet, and
  a second state (flowpath configuration) in which the at least one air intake is in fluid communication with the second air outlet and not the first air outlet.

In a further aspect, what is provided is an alternate nasal breathing apparatus that includes:
 at least one air intake;
 at least one air flow generator;
 a first air outlet and a second air outlet, wherein the first and second air outlets are sized, configured and mutually disposed for respective air delivery to a first nostril and a second nostril of a human user; and
 one or more actuatable valves operable to switch between
  a first state (flowpath configuration) in which a positive airflow is delivered to the first air outlet and not the second air outlet, and
  a second state (flowpath configuration) in which a positive airflow is delivered to the second air outlet and not the first air outlet.

In a still further aspect, what is provided is a method for delivering differential sensory stimulation to a human subject that includes the steps of:
 simultaneously,
  delivering air having a first temperature to one nostril of the human subject for inhalation by said nostril; and
  delivering air having a second temperature that is different than the first temperature to the other nostril of the human subject for inhalation by said nostril,
wherein the method is repeated over the course of multiple inhalations by the human subject.

In another aspect, what is provided is a method for delivering differential sensory stimulation to a human subject that includes the step of:
 during the course of a nasal inhalation by a human subject, for at least one nostril sequentially delivering air having different temperatures to said nostril for inhalation.

In still another aspect, what is provided is a method for topical sensory stimulation of a subject that includes the steps of:
 providing a positionable/movable air conduit having an air outlet end and an airstream moving therethrough and out said outlet end; and
 topically applying the airstream exiting the outlet end to different positions of the subject's body.

In a further aspect, what is provided is a method for topical sensory stimulation of a subject that includes the steps of:
 providing a first positionable/movable air conduit having an air outlet end and an airstream moving therethrough and out said outlet end;

providing a second positionable/movable air conduit having an air outlet end and an airstream moving therethrough and out said outlet end; and topically applying the airstreams exiting the outlet ends of the first and second positionable/movable air conduits to positions of the subject's body which are different and/or the same positions of application for the outlet ends of first and second positionable/movable air conduits.

In another aspect, what is provided is a method for topical sensory stimulation of a subject that includes the steps of:

providing a first air conduit having an air outlet end and an airstream moving therethrough and out said outlet end;

providing a second air conduit having an air outlet end and an airstream moving therethrough and out said outlet end; and topically applying the airstream exiting the first air conduit to the left external ear of the subject; and topically applying the airstream exiting the second air conduit to the right external ear of the subject.

The application of the airstreams to the external ears may be at least predominantly spatially restricted to the external ears (rather than being more broadly applied to the side of the head) or to one or more selected regions of the external ears.

In a still further aspect, what is provided is a method for topical sensory stimulation of a subject that includes the steps of:

for at least one topical position of a subject's body, such as but not limited to a topical position of the external ear, topically applying a first airstream having a first temperature to the position; and thereafter, topically applying a second airstream having a second temperature that is different than the first temperature to at least substantially the same position.

When the airstreams are topically applied to a particular position of the external ear, the application of the airstreams may be at least substantially or at least predominantly spatially restricted to that position rather than being more broadly applied to the external ear or beyond the external ear.

In another aspect, what is provided is a method for nasal breathing that includes the step of:

delivering a positive pressure airstream having a first pressure to a first nostril of a human user for inspiration, wherein simultaneously only air at ambient atmospheric pressure is inspired by or presented to the second nostril of the human user.

In still another aspect, what is provided is a method for nasal breathing that includes the steps of:

(i) delivering a positive pressure airstream to a first nostril of a human user for inspiration, wherein simultaneously only air at ambient atmospheric pressure is inspired by or presented to the second nostril of the human user; and thereafter (ii) delivering a positive pressure airstream to the second nostril of the human user for inspiration, wherein simultaneously only air at ambient atmospheric pressure is inspired by or presented to the first nostril of the human user.

Additional features, advantages, and embodiments may be set forth or apparent from consideration of the following detailed description, drawings, and claims.

DETAILED DESCRIPTION

In one aspect, the disclosure provides apparatuses for and related methods of delivering inhalation airstreams of different temperatures to the nostrils of a subject. Certain embodiments provide apparatuses for and related methods of alternately delivering inhalation airstreams of different temperatures to the respective nostrils of a subject.

Examples

An exemplary apparatus, shown in FIG. 1A, was constructed as follows. Two plastic pales 101 and 102 each having a volume of approximately 5 liters were provided. Two 10-foots lengths of silicone tubing (⅜ inch ID, 0.5 inch ID) 103 and 104 were provided. Each length of silicone tubing was coiled and disposed within a pale such that an air inlet end and an air outlet end of the tube remained disposed outside of the pale. One pale was then filled with cold water and ice, in order to cool air within the tube disposed therein (versus room temperature). The other pale was filled with hot water, in order to heat air within the tube disposed therein (versus room temperature). The pales were disposed adjacently on a table so that a seated individual (human subject) could direct cooled and heated air from the outlet ends of the tubes into different nostrils (N1, N2), and/or direct and topically apply the cooled and heated air, such as onto the face, neck and/or upper torso. The arrows in the figure show the direction of airflow through the tubes of the apparatus. In one configuration of the apparatus, no fan or air flow generator was operably connected. In this configuration, the outlet ends of the tubes were inserted substantially sealably into or against the nostrils of the subject so that air was drawn through the tubes by inhalation. This configuration was tested in an environment having an ambient air temperature of approximately 68° F. (or approximately 20° C.) and was found to be effective in separately delivering cooled and heated air to the nostrils.

Figure 1A:
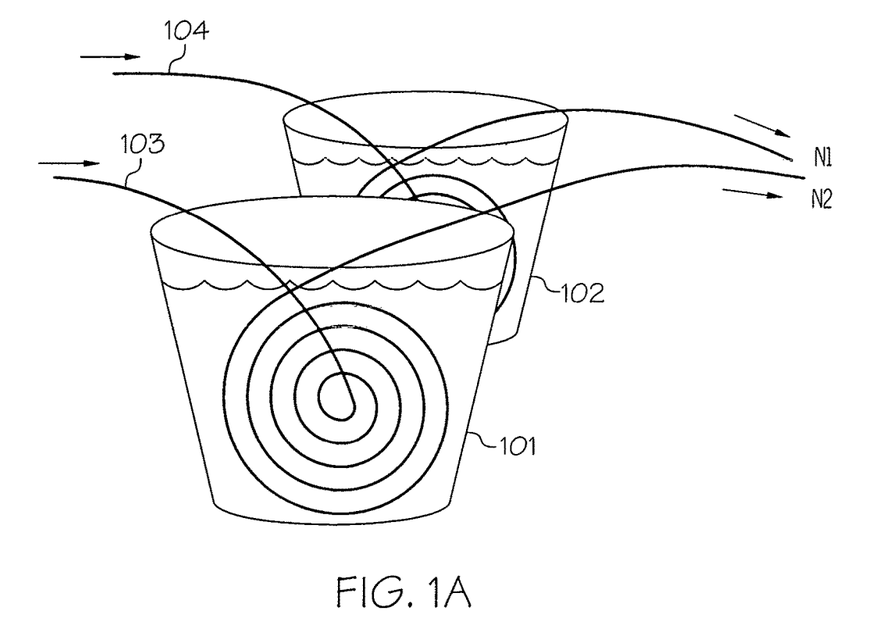
FIG. 1A shows an apparatus embodiment of the invention for providing cooled and heated airstreams for nasal inhalation by a user.
Figure 1B:
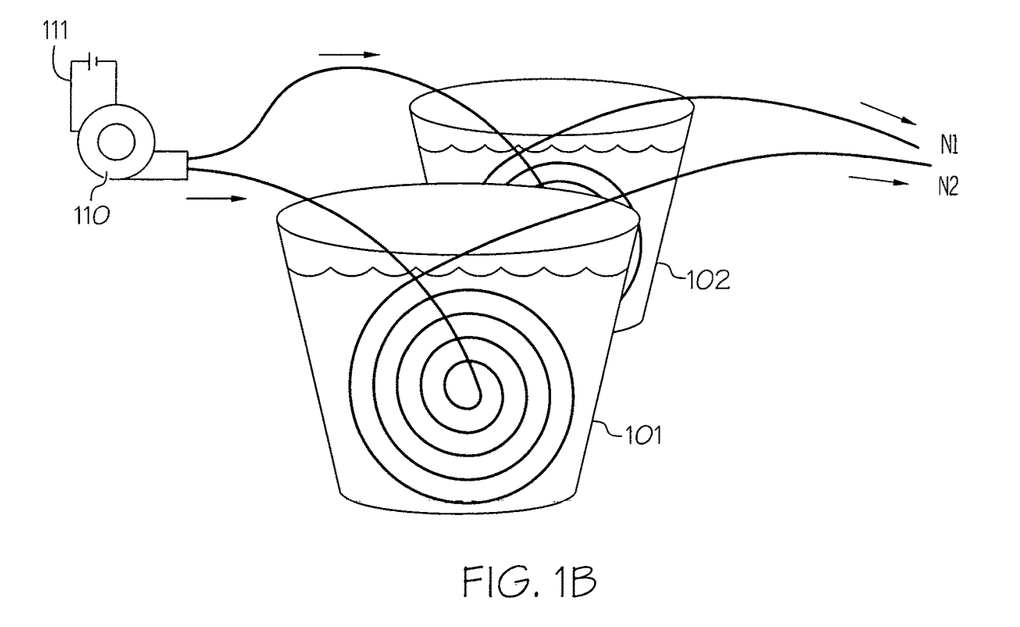
FIG. 1B shows an apparatus embodiment of the invention which is the embodiment shown in FIG. 1A modified by the addition of a centrifugal fan at the air inlet end to drive airflow toward and out of the air outlet end for nasal inhalation by a user or to otherwise provide cooled and heated airstreams such as for topical application to the skin of user.

In another configuration, shown in FIG. 1B, the air outlet of a small electric centrifugal fan 110, powered by a battery 111, was operably connected to the inlet end of each of the tubes to generate air flow through the tubes toward and out their outlet ends. This configuration was also tested in an environment having an ambient air temperature of approximately 68° F. (or approximately 20° C.) and was found to be effective in providing streams of cooled and heated air out of the respective tubes, which were separately delivered to the nostrils by insertion of the outlet ends of the tubes into the nostrils or by placing the outlet ends in proximity to the nostril openings so that each respective air stream was directed into one of the nostrils. The second configuration of the apparatus was also used to deliver streams of cooled and heated air to the skin of a subject (topically).

The following temperature alternating embodiments of the invention were also performed using the apparatuses shown in FIGS. 1A and 1B by manually switching the tubes between the nostrils during an exhalation (expiration). In one embodiment, switching is performed at selected or desired time periods, such as 1 minute, 2 minute, or 3 minute time periods. In another embodiment provided by the invention, switching is performed during every exhalation so that the temperature was alternated between nostrils upon every. In a further embodiment, switching is performed upon a preselected or desired number of exhalations, such as but not limited to 1, 2 or 3, so that the different temperature airstreams are already switched between the nostrils upon the following inhalation (inspiration).

Also provided are embodiments and variations in which one of the temperatures is ambient temperature, such as room temperature, and another temperature is either above or below the ambient temperature.

Temperature-controlled heated and refrigerated water baths commercially available from vendors such as ThermoFisher, VWR Scientific and others may, for example, be used for heating and cooling air as in the embodiments shown in FIGS. 1A and 1B. Further, while the constructed embodiments of FIGS. 1A and 1B effectively utilized continuous lengths of silicone rubber tubing, materials having high heat conductivity such as copper tubing or stainless steel tubing may, for example, be used at least for the heat transfer segments of the air conduits, i.e., the segments submerged in the water baths.

Figure 2:
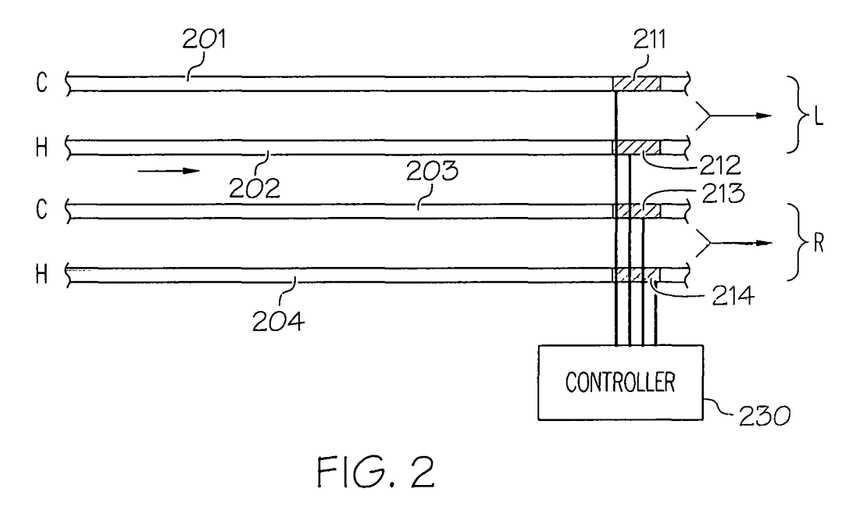
FIG. 2 shows an airflow control apparatus embodiment of the invention that employs actuatable on/off valves for independently controlling which of two airstreams, such as a cooled airstream and a heated airstream, is delivered to the left and right nostril of a user.
Figure 3:
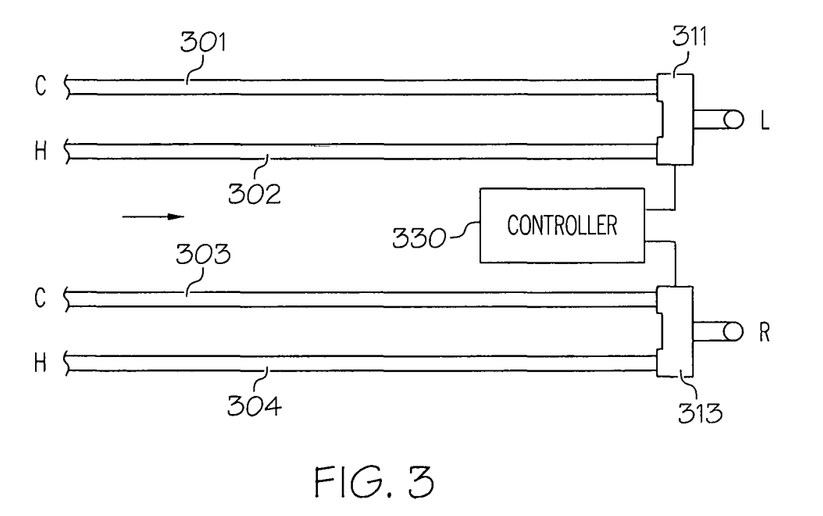
FIG. 3 shows an airflow control apparatus embodiment of the invention that employs actuatable three-way ball valves for independently controlling which of two airstreams, such as a cooled airstream and a heated airstream, is delivered to the left and right nostril of a user.

FIGS. 2-4 show air stream control embodiments for selectively delivering air from cooled and heated air streams to the left and right nostrils of a user. Only the air outlet portion of the complete apparatuses are shown in FIGS. 2-4, while the air stream cooling and heating portions which may, for example, be apparatuses as shown in FIGS. 1A and 1, are understood to be operably connected thereto. In addition, in FIGS. 2 and 3 where two heated air tubes/conduits and two cooled air tubes/conduits are shown, it should be understood that two separate tubes/conduits for each temperature may be provided side-by-side in apparatuses such as those shown in FIGS. 1A and 1B or the two tubes/conduits shown for each temperature may be bifurcated from the single tubes/conduits of apparatuses as shown in FIGS. 1A and 1B.

FIG. 2 shows an air stream control embodiment that includes a cooled air line 201 fluidly connected to a distal on/off valve 211 paired with a heated air line 202 fluidly connected to a distal on/off valve 212, for selective delivery of air to the left nostril of a user, and similarly a cooled air line 203 fluidly connected to a distal on/off valve 213 paired with a heated air line 204 fluidly connected to a distal on/off valve 214, for selective delivery of air to the right nostril of a user. Each of the on/off valves is independently actuatable by a controller 230. In one variation, the controller is configured or programmed to alternately provide cooled and heated air between the left and right nostrils of the user so that when the left nostril is receiving cooled air, the right nostril receives heated air and when the right nostril is receiving cooled air, the left nostril receives heated air. More generally, the air flow control configuration of the embodiment of FIG. 2 permits total control of which of the two different temperature air streams is delivered to a nostril at any one time, so that any combination is possible and also permits at any one time the mixing of the two different temperature air streams for one or both nostrils.

FIG. 3 shows an air stream control embodiment that includes a cooled air line 301 paired with a heated air line 302, each of 301 and 302 fluidly connected/couples at its distal end to a three-way ball valve 311, for selective delivery of cooled or heated air to the left nostril of a user, and similarly a cooled air line 303 with a heated air line 304, each of 303 and 304 fluidly connected/coupled its distal end to a three-way ball valve 313, for selective delivery of cooled or heated air to the right nostril of a user Each of valves 311 and 313 is independently actuatable by a controller 330. In one variation, the controller is configured or programmed to alternately provide cooled and heated air between the left and right nostrils of the user so that when the left nostril is receiving cooled air the right nostril receives heated air and when the right nostril is receiving cooled air the left nostril receives heated air. More generally, the air flow control configuration of this embodiment provides the following possible combinations of cooled (C) and heated (H) air streams with respect to left (L) and right (N) nostrils respectively: C-C, C-H, H-H, and H-C. These permutations are available when the three-way ball valves are L-type or T-type three-way ball valves. With T-type three-way ball valves, the valve can also be open to both heated and cooled air inlets at the same time to independently provide a blended temperature air stream to the left or right nostril.

Actuable valves used in the embodiments shown in FIGS. 2 and 3 and generally used in actuatably valved embodiments of the invention may, for example, be electrically actuated valves or hydraulically actuated valves. Valves other than ball valves may also be used, such as solenoid valves and solenoid-driven slider valves, e.g., 2-way and/or 3-way solenoid-driven slider valves, e.g., from Takasago Fluidic Systems (Westborough, Massachusetts, USA).

Generally, to provide automated actuatably valved embodiments, dedicated and/or programmable control circuitry may be used to control actuation of the valves and any supporting hardware.

Figure 4A:
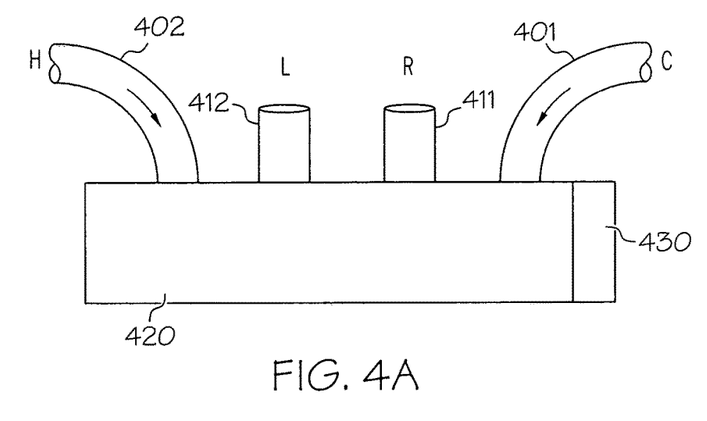
FIGS. 4A-D illustrate an airflow control apparatus embodiment of the invention that includes a ported tubular casing enclosing a cylindrical manifold in which different air flow conduits formed in the manifold fluidly couple-to/engage-with the ports of the casing depending on the rotational position of the manifold within the casing, to alternately respectively deliver two airstreams, such as a cooled airstream and a heated airstream, to the left and right nostrils of a user.
Figure 4B:
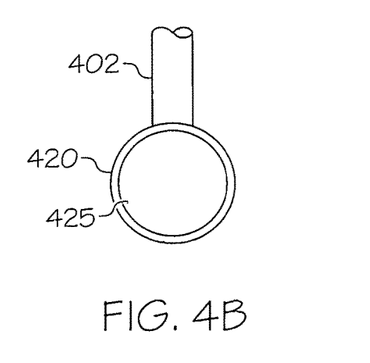
Figure 4C:
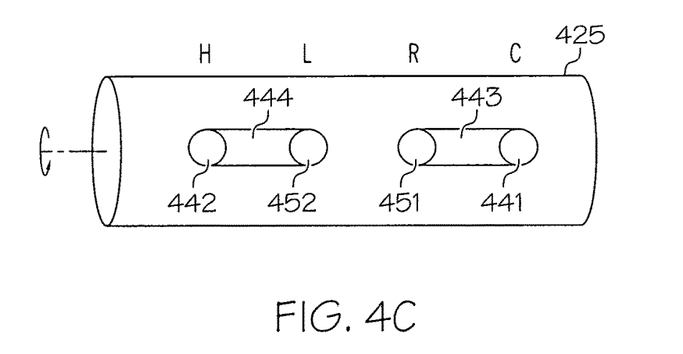
Figure 4D:
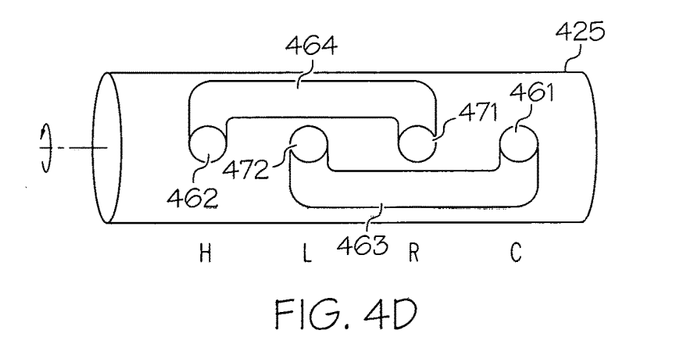
Figure 5A:
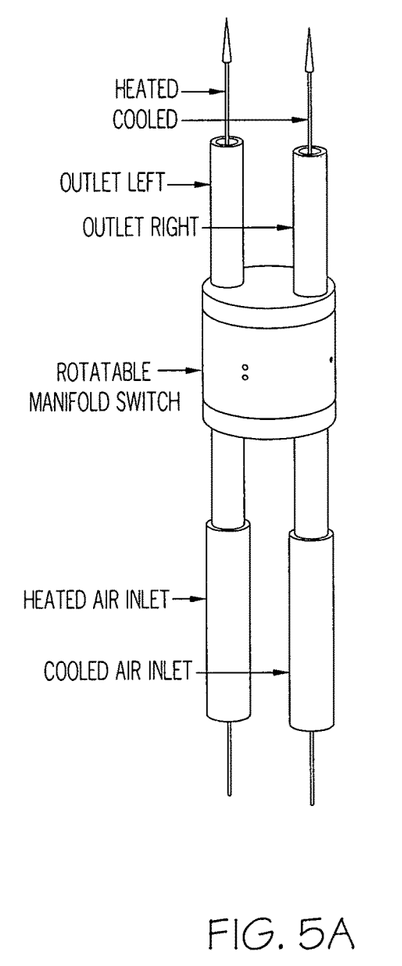
FIGS. 5A-E illustrate another airflow control apparatus embodiment of the invention that includes a cylindrical manifold for switching air distribution from two inlet airstreams between two airstream outlets by rotating the manifold.
Figure 5B:
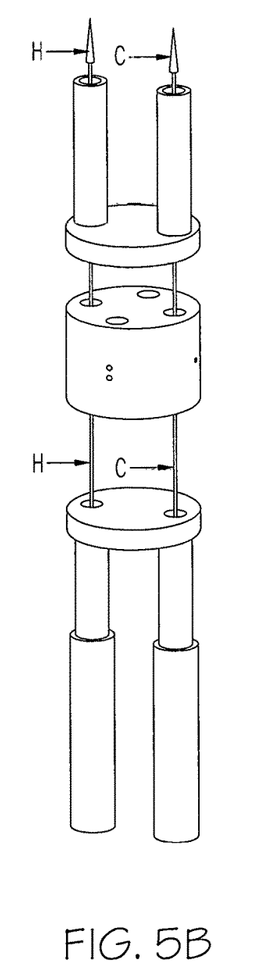
Figure 5C:
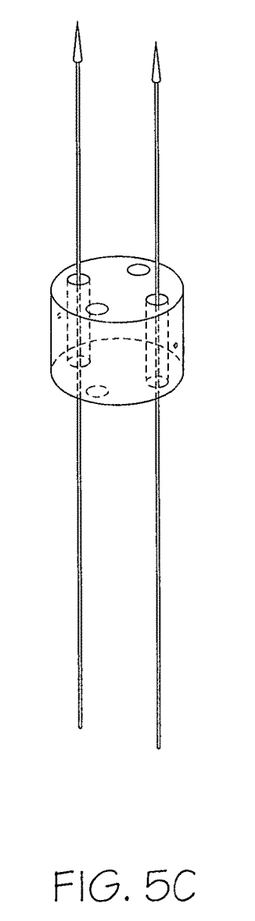
Figure 5D:
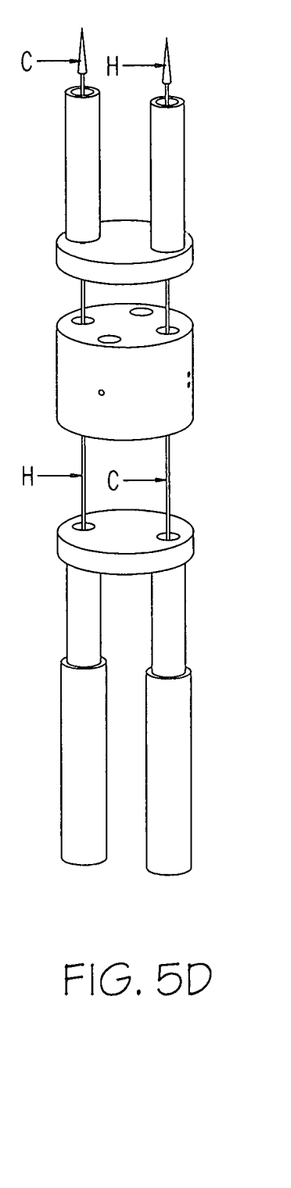
Figure 5E:
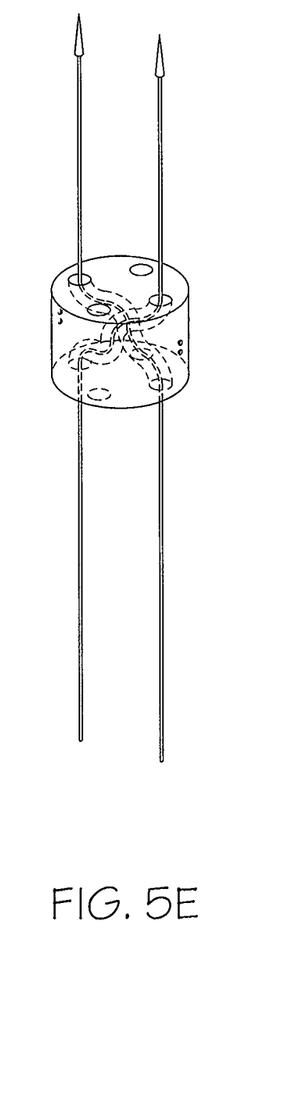

FIGS. 4A-4D illustrate an air flow control embodiment of the invention in which a ported tubular casing encloses a cylindrical manifold in which different air flow conduits formed in the manifold fluidly couple-to/engage the ports of the casing depending on the rotational position of the manifold within the casing, to selectively deliver heated or cooled air to the left and right nostril/outlet respectively. FIG. 4A shows a side view of ported tubular casing 420 with cooled air inlet port 401, heated air inlet port 402, right outlet/nostril port 411 and left outlet nostril port 412. 430 is a manual dial or a motor, such as a disc motor, that is secured to case 420 and operably connected to rotate encased cylindrical manifold (425). The motor may, for example, be a step motor. When 420 is a motor, it may be connected to a controller and power source (not shown). FIG. 4B shows a left end-wise view of the device with cylindrical manifold 425 disposed within tubular ported casing 420. FIG. 4C shows one side of cylindrical manifold 425 in detail with a first internal channel (air passageway) 444 opening in apertures 442 and 452 at the surface of the manifold formed therein, and a second internal channel (air passageway) 443 opening in apertures 441 and 451 at the surface of the manifold formed therein. Apertures 442, 452, 451 and 441 are aligned and can be brought into register and respective fluid communication with ports 402, 412, 411 and 401 of the casing through rotation of manifold 425. In this position, heated air provided by inlet port 402 is directed through channel 444 to outlet port 412, and cooled air provided by inlet port 401 is directed to through channel 443 to outlet port 411. To switch the airstreams delivered to the outlet ports, manifold 425 can be rotated to its other side (shown in FIG. 4D) so that the channels shown in FIG. 4D direct the air flow. FIG. 4D shows a first internal channel 464 opening in apertures 462 and 471 at the surface of the manifold formed therein, and a second internal channel 463 opening in apertures 472 and 461 at the surface of the manifold formed therein. Apertures 462, 472, 471 and 461 are aligned and can be brought into register and respective fluid communication with ports 402, 412, 411 and 401 of the casing through rotation of manifold 425. In this position, heated air provided by inlet port 402 is directed through channel 464 to right outlet port 411 and cooled air provided by inlet port 401 is directed through channel 463 to left outlet port 412. Thus, by rotationally switching between two positions of manifold 425, this embodiment permits alternation between two states of airflow, cooled air to the left outlet/nostril with heated air to the right outlet/nostril, and cooled air to the right outlet/nostril with heated air to the left outlet/nostril. It should however be appreciated that a manifold in which further registers of channels are formed can be readily provided as further embodiments of the invention for providing H:H and/or C:C, in addition to H:C and C:H permutations. Additional or alternative registers that blend (converge) air from the two inlets for delivery to one or both of the outlets may also be provided.

FIGS. 5A-E illustrate another airflow control apparatus embodiment of the invention that includes a cylindrical manifold for switching the distribution of two inlet airstreams between two airstream outlets by rotating the manifold. The manifold may be rotatably mounted on an axle (not shown) disposed along its central longitudinal axis and supported by the top plate and bottom plate, which plates may be rigidly connected to each other by one or more brackets (not shown) to prevent relative motion between the plates. The brackets may further support a motorized drive mechanism operably linked to the manifold and under control of a controller to effect rotation of the manifold.

Rotatable valve manifold embodiments such as that exemplified in FIGS. 4A-D and 5A-E can be readily manufactured from metallic and/or rigid polymeric materials by conventional manufacturing techniques such as machining and/or additive manufacturing.

Embodiments that include actuatable valves under the control of a controller (control circuitry), such as but not limited to apparatuses including the airflow control sub-apparatuses shown in FIGS. 2-4, may, in a similar manner as some modern ventilators, further include pressure and/or airflow sensors operably linked to the controller, which sensors may be disposed, for example, distal to the valves (on the user side of the valves) to detect the change from inspiratory phase to expiratory phase and/or expiratory phase to inspiratory phase by a user and/or in general the point in the respiratory cycle, and the controller may be configured to actuate the valves based, at least in part, on the respiratory cycle as determined using input from the sensors according to a routine or program, whether fixed, semi-random or random. For example, such a system may be configured to actuate the valves during every expiration to switch different temperature airstreams between left and right nostrils for every inspiration, or configured to make the same switch during every other expiration, or configured to switch the airstream delivered to one or both nostrils during an inspiration if a particular airflow control sub-apparatus permits, or configured to provide any airflow patterns or permutations permitted by an airflow control sub-apparatus.

Valved embodiments, such as those shown in FIGS. 2-4, may optionally include in one or more of the airline tubes on the proximal side (the air supply side) of the valve one or more leak holes/passageways formed therethrough. The purpose of the leak holes/passageways is to keep air from the heated or cooled air source continuously flowing through the respective proximal length of the tube when the valve is closed so that the air available to pass the valve when the valve is opened is more freshly/immediately provided by the respective air source.

While the embodiments exemplified in FIGS. 1A and 1B utilize conductive heat transfer to heat and cool respective airstreams, any suitable types of heating and cooling mechanisms and elements may be used alone or in combination. For example, vapor-compression cycle (refrigerant-based) mechanisms, such as those used in conventional residential air conditioning units, may be used to provide both a heated and cooled airstream versus an ambient environmental temperature. Similarly, thermoelectric effect devices such as Peltier effects devices may be used to provide both a heated and cooled airstream versus an ambient environmental temperature. With respect to cooling, free cooling may for example, be used. With respect to heating, Joule heating, also known as Ohmic heating and resistive heating, may, for example, be used.

Embodiments of the disclosure may, for example, use atmospheric air only. Further embodiments may, for example, utilize atmospheric air supplemented with oxygen. Supplemental oxygen may, for example, be provided from a tank or an oxygen generator.

A user or subject may be a human user or subject, or a non-human mammal user or subject.

In one variation, the methods of the disclosure are performed while the user/subject is awake, i.e., not asleep. The methods may, for example, be performed in a session in which the user is awake for the entire duration of the session. In another variation, the methods of the invention are not performed for/by a user in a period spanning wakefulness and sleep. In a further variation, the methods of the disclosure may be performed for/by a user in a period spanning wakefulness and sleep. In another variation, the methods of the invention may be performed for/by a user during sleep.

In another variation, the methods of the disclosure are not performed while the user/subject is under or receiving anesthesia.

In further variation, the methods of the disclosure are not performed while the user/subject is undergoing or receiving a surgical procedure.

The methods of the disclosure may, for example, be performed for at least 5 minutes, for at least 10 minutes, for at least 15 minutes, for at least 20 minutes, for at least 30 minutes, for at least 60 minutes, for at least 90 minutes, or for at least 120 minutes. A session of performing any of the methods of the invention may, for example, have a duration of at least 5 minutes, at least 10 minutes, at least 15 minutes, at least 20 minutes, at least 30 minutes, at least 60 minutes, at least 90 minutes, or at least 120 minutes. The methods of the invention may, for example, be performed for a duration in the range of 5-120 minutes or any subrange or number of minutes in said range.

The methods of the disclosure may, for example, be performed once per day or multiple times per day. The methods of the disclosure may, for example, be performed for multiple days such as every day or every other day over the course of multiple days, such as for at least 4 days, at least 1 week, at least two weeks, at least 3 weeks, or at least 4 weeks.

In another variation, the user/subject does not have or suffer from a respiratory disease or respiratory disorder. In a related variation, the user does not have or suffer from, at the time of use, a respiratory disease or respiratory disorder. In another variation, the user does not suffer from difficulty breathing. In a further variation, the user does not have or suffer from sleep apnea. In another variation, the user does not have or suffer from COPD.

The apparatus and method embodiments of the disclosure may, for example, be used to induce, promote and/or aid in relaxation or calming, to reduce stress, to reduce anxiety, and/or to treat a number of disorders including but not limited to attention deficit disorder (ADD) in adults and/or children, attention deficit hyperactivity disorder (ADHD) in adults and/or children, post-traumatic stress disorder (PTSD), anxiety, and anxiety disorders.

The apparatus and method embodiments of the disclosure may, for example, be used by a user to improve the performance of an attention-requiring task or activity by the user. In one variation, the apparatus and method embodiments of the invention may, for example, be used by the user during the performance of an attention-attention-requiring task or activity to improve the user's performance of the task or activity. The user may, for example, suffer from an attention deficit and/or may, for example, have ADD or ADHD.

Without limitation, the following apparatuses, methods and embodiments thereof are also disclosed.

Embodiment 1. An apparatus for asymmetric temperature nostril breathing that includes:
  a first air source of air having a first temperature;
  a second air source of air having a second temperature, wherein the first temperature and the second temperature are different;
  a first air conduit including a first air outlet, said first air conduit configured to deliver air from the first air source to the first air outlet; and
  a second air conduit including a second air outlet, said second air conduit configured to deliver air from the second air source to the second air outlet,
  wherein the apparatus is configured to simultaneously deliver air from the first air conduit to the first air outlet and air from the second air source to the second air outlet.

Embodiment 2. An apparatus for asymmetric temperature nostril breathing that includes:
  an air heating element (an air heating unit such as an air heater);
  an air cooling element (an air cooling unit such as an air cooler);
  a first air conduit having an air inlet and in fluid communication with a first air outlet, configured to deliver air heated by the air heating element therethrough; and
  a second air conduit having an air inlet and in fluid communication with a second air outlet, configured to deliver air cooled by the air cooling element therethrough,
  wherein the apparatus is configured to simultaneously deliver air heated by the air heating element through the first air conduit and air cooled by the air cooling element through the second air conduit.

Embodiment 3. The apparatus of embodiment 1 or 2, further including at least one air flow generator configured to generate air flow in the first and second air conduits toward and out the air outlets.

Embodiment 4. The apparatus of embodiment 3, wherein the at least one air flow generator includes at least one electric fan.

Embodiment 5. The apparatus of embodiment 1 or 2, wherein the apparatus does not include an air flow generator.

Embodiment 6. The apparatus of any one of the preceding embodiments, wherein at least a section of each of the air conduits near its air outlet end is flexible.

Embodiment 7. The apparatus of embodiment 6, wherein at least a section of each of the air conduits near its air outlet end includes flexible tubing.

Embodiment 8. The apparatus of any one of the preceding embodiments, wherein each of the air outlets is sized and configured such that the cross section of the airstream exiting the air outlet is equal to or less than 3.14 cm$^2$, equal to or less than 2.41 cm$^2$, equal to or less than 0.79 cm$^2$, equal to or less than 0.2 cm$^2$, or any positive values or subranges of area within any of the preceding.

Embodiment 9. The apparatus of embodiment 8, wherein each of other air outlets is sized and configured such the cross section of the airstream exiting the air outlet has an area of at least 0.00785 cm$^2$ (0.785 mm$^2$).

Embodiment 10. The apparatus of any one of the preceding embodiments, further including means for switching the airstreams delivered to the air outlets.

Embodiment 11. The apparatus of any one of embodiments 1-9, further including means for alternating the airstreams delivered to the air outlets.

Embodiment 12. The apparatus of any one of the preceding embodiments, wherein the first and second air outlets are sized and configured to respectively deliver air to a first and a second nostril of a human user.

Embodiment 13. The apparatus of any one of the preceding embodiments, wherein the first and second air outlets are sized and configured for respective insertion into a first and a second nostril of a human user.

Embodiment 14. The apparatus of any one of the preceding embodiments, wherein the first and second air outlets are sized, configured and disposed to respectively and at least substantially mutually exclusively deliver air to a first and a second nostril of a human user.

Embodiment 15. The apparatus of any one of the preceding embodiments, wherein the first and second air outlets are respectively disposed in proximity to a first and second nostril of a human user but not inserted into the nostrils of the human user.

Embodiment 16. The apparatus of any one embodiments 1-14, wherein the first and second air outlets are respectively inserted into a first and second nostril of a human user.

Embodiment 17. An alternate nasal breathing apparatus that includes:
at least one air intake;
a first air outlet and a second air outlet, wherein the first and second air outlets are sized, configured and mutually disposed for respective at least substantially sealable insertion into a first nostril and a second nostril of a human user; and
one or more actuatable valves operable to switch between
a first state (flowpath configuration) in which the at least one air intake is in fluid communication with the first air outlet and not the second air outlet, and
a second state (flowpath configuration) in which the at least one air intake is in fluid communication with the second air outlet and not the first air outlet.

Embodiment 18. The alternate nasal breathing apparatus of embodiment 17, further including:
a controller operably linked to operate the one or more valves to switch between the two states.

Embodiment 19. The alternate nasal breathing apparatus of embodiment 18, wherein the controller is configured to automatically alternate between the two states.

Embodiment 20. The alternate nasal breathing apparatus of any one of embodiments 17-19, wherein the apparatus does not include an air flow generator.

Embodiment 21. The alternate nasal breathing apparatus of any one of embodiments 17-19, wherein the apparatus further includes at least one air flow generator.

Embodiment 22. An alternate nasal breathing apparatus that includes:
at least one air intake;
at least one air flow generator;
a first air outlet and a second air outlet, wherein the first and second air outlets are sized, configured and mutually disposed for respective air delivery to a first nostril and a second nostril of a human user; and
one or more actuatable valves operable to switch between
a first state (flowpath configuration) in which a positive airflow is delivered to the first air outlet and not the second air outlet, and
a second state (flowpath configuration) in which a positive airflow is delivered to the second air outlet and not the first air outlet.

Embodiment 23. The alternate nasal breathing apparatus of embodiment 22, further including:
a controller operably linked to operate the one or more valves to switch between the two states.

Embodiment 24. The alternate nasal breathing apparatus of embodiment 23, wherein the controller is configured to automatically alternate between the two states.

Embodiment 25. A method for delivering differential sensory stimulation to a human subject that includes the steps of:
simultaneously,
delivering air having a first temperature to one nostril of the human subject for inhalation by said nostril; and
delivering air having a second temperature that is different than the first temperature to the other nostril of the human subject for inhalation by said nostril,
wherein the method is repeated over the course of multiple inhalations by the human subject.

Embodiment 26. The method of embodiment 25, wherein the delivery of air having the first temperature and the delivery of air having the second temperature is switched between nostrils of the subject at least one time over said course of multiple inhalations.

Embodiment 27. The method of embodiment 25, wherein the delivery of air having the first temperature and the delivery of air having the second temperature is alternated between nostrils of the subject.

Embodiment 28. The method of embodiment 27, wherein the delivery of air having the first temperature and the delivery of air having the second temperature is alternated between nostrils of the subject for consecutive inhalations by the subject.

Embodiment 29. The method of embodiment 25, wherein the delivery of air having the first temperature and the delivery of air having the second temperature is switched between nostrils of the subject at preselected time intervals.

Embodiment 30. The method of any one of embodiments 25-29, wherein
the method is performed in an environment having an ambient temperature;
the first temperature is below the ambient temperature; and
the second temperature is above the ambient temperature.

The first temperature and the second temperature may, for example, differ by at least 20 degrees Fahrenheit.

Embodiment 31. A method for delivering differential sensory stimulation to a human subject that includes the step of:
during the course of a nasal inhalation by a human subject, for at least one nostril sequentially delivering air having different temperatures to said nostril for inhalation.

Embodiment 32. The method of embodiment 31, wherein the method is repeated over the course of multiple inhalations by the human subject.

Embodiment 33. The method of embodiment 31 or 32, wherein the delivering step includes:
during the course of a nasal inhalation by a human subject, for each nostril sequentially delivering air having different temperatures to the nostril for inhalation.

Embodiment 34. The method of embodiment 33, wherein air of the same temperature is delivered to each of the nostrils at the same times during an inhalation Embodiment 35. The method of embodiment 33, wherein air having different temperatures is simultaneously respectively delivered to the nostrils of the subject during an inhalation.

Embodiment 36. The method of embodiment 35, wherein the delivery of air having different temperatures is synchronously switched between the nostrils of the subject.

Embodiment 37. The method of any one of embodiments 31-36, wherein
the method is performed in an environment having an ambient temperature; and the air having different temperatures includes air having a first temperature below the ambient temperature and air having a second temperature above the ambient temperature.

Embodiment 38. A method for topical sensory stimulation of a subject that includes the steps of:
providing a positionable/movable air conduit having an air outlet end and an airstream moving therethrough and out said outlet end; and
topically applying the airstream exiting the outlet end to at least one position of the subject's body, such as different positions of the subject's body.

Embodiment 38.1. The method of claim 38.1, wherein the step of providing the positionable/movable air conduit further comprises providing an airflow generator operably connected to the positionable/movable air conduit to provide airflow therethrough and out said outlet end.

Embodiment 39. The method of embodiment 38 or 38.1, wherein the cross section of the airstream exiting the outlet end is equal to or less than 3.14 cm$^2$, equal to or less than 2.41 cm$^2$, equal to or less than 0.79 cm$^2$, equal to or less than 0.2 cm$^2$, or any positive values or subranges of area within any of the preceding.

Embodiment 40. The method of embodiment 39, wherein the cross section of the airstream exiting the outlet end has an area of at least 0.00785 cm$^2$ (0.785 mm$^2$).

Embodiment 41. The method of any one of embodiments 38-40, wherein the air conduit includes a tube.

Embodiment 42. The method of any one of embodiments 38-41, wherein the tube is a flexible tube.

Embodiment 43. The method of any one of embodiments 38-42, wherein the outlet end of the tube is positioned 5 cm or less from the surface of the subject's body during performance of the method.

Embodiment 44. The method of any one of embodiments 38-43, wherein the step of topically applying the airstream exiting the outlet end to different positions of the subject's body includes continuously topically applying the airstream exiting the outlet end to the subject's body by moving the outlet end over an area of the subject's body.

Embodiment 45. The method of any one of embodiments 38-44, wherein the method is performed in an environment having an ambient temperature and the temperature of the airstream exiting the outlet end is within plus/minus 5 degrees Celsius of the ambient temperature.

Embodiment 46. The method of any one of embodiments 38-44, wherein the method is performed in an environment having an ambient temperature and the temperature of the airstream exiting the outlet end is less than the ambient temperature.

Embodiment 47. The method of embodiment 46, wherein the temperature of the airstream exiting the outlet end is at least 10° F. (or at least 5.56° C.), at least 20° F. (or at least 11.13° C.), at least 30° F. (or at least 16.68° C.), at least 40° F. (or at least 22.24° C.), or at least 50° F. (or at least 27.8° C.) less than the ambient temperature.

Embodiment 48. The method of any one of embodiments 38-44, wherein the method is performed in an environment having an ambient temperature and the temperature of the airstream exiting the outlet end is greater than the ambient temperature.

Embodiment 49. The method of embodiment 48, wherein the temperature of the airstream exiting the outlet end is at least 10° F. (or at least 5.56° C.), at least 20° F. (or at least 11.13° C.), at least 30° F. (or at least 16.68° C.), at least 40° F. (or at least 22.24° C.), or at least 50° F. (or at least 27.8° C.) greater than the ambient temperature.

Embodiment 49.1. The method of any one of embodiments 38-49, wherein air from the outlet end of the conduit is topically applied to one or more locations/positions of a part of the subject's body, for example, an arm, a leg, a hand, a foot, front torso, back torso, face, side of face, an ear (the external ear, including or excluding the outer ear canal), or neck.

Embodiment 49.2. The method of any one of embodiments 38-49, wherein air from the outlet end of the conduit is topically applied to one or both ears.

Embodiment 49.3. The method of embodiment 49.2, wherein for each of the one or both ears, air from the outlet end of the conduit is topically applied to one or more of the vagus nerve region (VNR), auriculotemporal nerve region (ATNR), and great auricular nerve region (GANR).

Embodiment 50. A method for topical sensory stimulation of a subject that includes the steps of:
providing a first positionable/movable air conduit having an air outlet end and an airstream moving therethrough and out said outlet end;
providing a second positionable/movable air conduit having an air outlet end and an airstream moving therethrough and out said outlet end; and
topically applying the airstreams exiting the outlet ends of the first and second positionable/movable air conduits to positions of the subject's body, wherein said positions are different positions and/or the same positions of application for the outlet ends of first and second positionable/movable air conduits.

Embodiment 50.1. The method of claim 38.1, further comprising providing an airflow generator operably connected to each positionable/movable air conduit to provide airflow therethrough, which airflow generator may be the same airflow generator or a separate airflow generator for each of the first and second positionable/movable air conduits.

Embodiment 51. The method of embodiment 50 or 50.1, wherein the step of topically applying the airstreams exiting the outlet ends of the first and second conduits to positions of the subject's body include continuously topically applying the airstreams exiting said outlet ends to the subject's body by moving the outlet ends over an area of the subject's body.

Embodiment 52. The method of embodiment 50 or 51, wherein the step of topically applying the airstreams exiting the outlet ends of the first and second conduits to positions of the subject's body include continuously topically applying the airstreams exiting said outlet ends to the subject's body by moving the outlet ends over an area of the subject's body such that the paths of air application by the two outlet ends at least sometimes cross.

Embodiment 53. The method of any one of embodiments 50-52, wherein airstreams from the outlet ends of the first and second conduits are non-simultaneously topically applied, such as sequentially topically applied, to same positions of the subject's body and/or positions separated by no more than 1 cm, such as positions separated by no more than 0.5 cm.

Embodiment 54. The method of any one of embodiments 50-53, wherein airstreams from the outlet ends of the first and second conduits are simultaneously topically applied to different positions of the subject's body, such as but not limited to different positions that are within 10 cm of each other, for example, within 7 cm, within 5 cm, or within 3 cm of each other. In one variation, the different positions are separated by at least 0.25 cm, 0.5 cm, or 1.0 cm.

Embodiment 55. The method of any one of embodiments 50-54, wherein air from the outlet ends of the first and second air conduits is respectively, simultaneously or sequentially, topically applied from the outlet ends of the first and second conduits to different locations/positions of the same part of the subject's body, for example, an arm, a leg, a hand, a foot, front torso, back torso, face, side of face, an ear (the external ear, including or excluding the outer ear canal), or neck.

Embodiment 55.1. The method of embodiment 55, wherein the body part is an ear and wherein air from one or both of the outlet ends of the first and second conduits is topically applied to one or more of the vagus nerve region (VNR), auriculotemporal nerve region (ATNR), and great auricular nerve region (GANR) of the ear.

Embodiment 55.2. The method of any one of embodiments 50-54, wherein the subject has a left ear and a right ear, and air from the outlet ends of the first and second air conduits is respectively topically applied to the two ears (the external ears, including or excluding the outer ear canals) such that one outlet end directs air onto one ear and the other outlet end directs air onto the other ear.

Embodiment 55.3. The method of embodiment 55.2, wherein for an ear, air from the respective outlet end is topically applied to one or more of the vagus nerve region (VNR), auriculotemporal nerve region (ATNR), and great auricular nerve region (GANR) of the ear.

Embodiment 56. The method of any one of embodiments 50-55, wherein the cross section of the airstream exiting the outlet end of each of the first and second conduits is equal to or less than 3.14 cm$^2$, equal to or less than 2.41 cm$^2$, equal to or less than 0.79 cm$^2$, equal to or less than 0.2 cm$^2$, or any positive values or subranges of area within any of the preceding.

Embodiment 57. The method of embodiment 56, wherein the cross section of the airstream exiting the outlet end of each of the first and second conduits has an area of at least 0.00785 cm$^2$ (0.785 mm$^2$).

Embodiment 58. The method of any one of embodiments 50-57, wherein each of the first and second air conduits includes a tube.

Embodiment 59. The method of embodiment 58, wherein the tube is a flexible tube.

Embodiment 60. The method of any one of embodiments 50-59, wherein the outlet ends of the first and second air conduits are positioned 5 cm or less from the surface of the subject's body during performance of the method.

Embodiment 61. The method of any one of embodiments 50-60, wherein the method is performed in an environment having an ambient temperature and the temperature of the airstream exiting the outlet end of at least one of the first and second air conduits is within plus/minus 5 degrees Celsius of the ambient temperature.

Embodiment 62. The method of any one of embodiments 50-60, wherein the temperatures of the airstreams exiting the outlet ends of the first and second air conduits are different.

Embodiment 63. The method of embodiment 62, wherein the method is performed in an environment having an ambient temperature, wherein the temperature of the airstream exiting the outlet end of the first air conduit is greater than the ambient temperature, and wherein the temperature exiting the outlet end go the second air conduit is less than the ambient temperature.

Embodiment 64. The method of embodiment 63, wherein
the temperature of the airstream exiting the outlet end of the first air conduit is at least 10° F. (or at least 5.56° C.), at least 20° F. (or at least 11.13° C.), at least 30° F. (or at least 16.68° C.), at least 40° F. (or at least 22.24° C.), or at least 50° F. (or at least 27.8° C.) greater than the ambient temperature; and
the temperature of the airstream exiting the outlet end of the second air conduit is at least 10° F. (or at least 5.56° C.), at least 20° F. (or at least 11.13° C.), at least 30° F. (or at least 16.68° C.), at least 40° F. (or at least 22.24° C.), or at least 50° F. (or at least 27.8° C.) less than the ambient temperature.

Embodiment 65. A method for topical sensory stimulation of a subject that includes the steps of:
for at least one topical position of a subject's body,
topically applying a first airstream having a first temperature to the position; and
thereafter, topically applying a second airstream having a second temperature that is different than the first temperature to at least substantially the same position.

Embodiment 66. The method of embodiment 65, wherein the method is performed in an environment of ambient temperature and at least one of the first and second temperatures is different than the ambient temperature.

Embodiment 67. The method of embodiment 66, wherein each of the first and second temperatures are different than the ambient temperature.

Embodiment 68. The method of embodiment 65, wherein
(i) the first temperature is less than the ambient temperature and the second temperature is greater than the ambient temperature; or
(ii) the first temperature is greater than the ambient temperature and the second temperature is less than the ambient temperature.

Embodiment 69. The method of embodiment 68, wherein
the temperature that is less than the ambient temperature is at least 10° F. (or at least 5.56° C.), at least 20° F. (or at least 11.13° C.), at least 30° F. (or at least 16.68° C.), at least 40° F. (or at least 22.24° C.), or at least 50° F. (or at least 27.8° C.) less than the ambient temperature; and
the temperature that is greater than the ambient temperature is at least 10° F. (or at least 5.56° C.), at least 20° F. (or at least 11.13° C.), at least 30° F. (or at least 16.68° C.), at least 40° F. (or at least 22.24° C.), or at least 50° F. (or at least 27.8° C.) greater than the ambient temperature.

Embodiment 70. The method of any one of embodiments 65-69, performed for a plurality of topical positions of the subject's body.

Embodiment 71. The method of embodiment 70, simultaneously performed for a plurality of topical positions of the subject's body.

Embodiment 72. The method of any one of embodiments 65-71, wherein the at least one topical position includes more than one topical position on the same part of the subject's body such as but not limited to an arm, a leg, a hand, a foot, front torso, back torso, face, side of face, an ear (the external ear, including or excluding the outer ear canal), or neck.

Embodiment 72.1 The method of any one of embodiments 65-72, wherein the at least one topical position of the subject's body includes a topical position of an ear (the external ear, including or excluding the outer ear canal).

Embodiment 72.2 The method of any one of embodiments 65-72.1, wherein the subject has a left ear and a right ear and the at least one topical position of the subject's body includes a topical position of the left ear (the external ear, including or excluding the outer ear canal) and a topical position of the right ear (the external ear, including or excluding the outer ear canal).

Embodiment 72.3. The method of embodiment 72.2, wherein airstreams are simultaneously applied to corresponding positions on the left ear and the right ear of the subject.

Embodiment 72.4. The method of embodiment 72.2, wherein airstreams are simultaneously applied to different positions on the left ear and the right ear of the subject.

Embodiment 72.5. The method of embodiment 72.3 or 72.4, wherein the airstreams simultaneously applied to the left and right ears have at least substantially different temperatures.

Embodiment 72.6. The method of embodiment 72.3 or 72.4, wherein the airstreams simultaneously applied to the left and right ears have at least substantially the same temperatures.

Embodiment 72.7. The method of any one of embodiments 72.1-72.6, wherein the topical position of an ear is within the vagus nerve region (VNR), the auriculotemporal nerve region (ATNR), or the great auricular nerve region (GANR) of the ear.

Embodiment 73. A method for nasal breathing that includes the step of.
  delivering a positive pressure airstream having a first pressure to a first nostril of a human user for inspiration,
  wherein simultaneously only air at ambient atmospheric pressure is inspired by or presented to the second nostril of the human user.

Embodiment 74. A method for nasal breathing that includes the steps of.
  (i) delivering a positive pressure airstream to a first nostril of a human user for inspiration,
  wherein simultaneously only air at ambient atmospheric pressure is inspired by or presented to the second nostril of the human user; and thereafter
  (ii) delivering a positive pressure airstream to the second nostril of the human user for inspiration,
  wherein simultaneously only air at ambient atmospheric pressure is inspired by or presented to the first nostril of the human user.

Embodiment 75. The method of embodiment 74, wherein steps (i) and (ii) are repeatedly performed in succession.

Embodiment 76. The method of embodiment 74 or 75, wherein the positive pressure airstream delivered in step (i) and the positive pressure airstream delivered in step (ii) have at least substantially the same pressure.

Embodiment 77. The method of embodiment 74 or 75, wherein the positive pressure airstream delivered in step (i) and the positive pressure airstream delivered in step (ii) have different pressures.

Embodiment 78. Any one of the preceding embodiments, wherein the user/subject does not have or suffer from sleep apnea and/or COPD and/or the apparatus is not for treatment of sleep apnea and/or COPD.

Embodiment 79. Any one of the preceding embodiments, wherein the user/subject does not have or suffer from a respiratory disease or respiratory disorder and/or the apparatus is not for treatment of a respiratory disease or respiratory disorder.

Embodiment 80. Any one of the preceding method embodiments, wherein the user/subject does not have or suffer from a respiratory disease or respiratory disorder at the time the method is performed.

Embodiment 81. Any one of the preceding embodiments, wherein the embodiment is for inducing, promoting and/or aiding in relaxation or calming, for reducing stress, for reducing or treating anxiety, and/or for treating a disorder which is attention deficit disorder (ADD) such as in an adult or child, attention deficit hyperactivity disorder (ADHD) such as in an adult or child, post-traumatic stress disorder (PTSD), anxiety, or an anxiety disorder for a subject such as human user in need thereof.

Embodiment 81.1 Any one of the preceding embodiments, wherein the embodiment is for the treatment or prevention of any one or more of: headache including but not limited to migraine headache or cluster headache; depression; epilepsy and epileptic seizures.

Embodiment 81.2 Any one of the preceding nasal breathing apparatus or method embodiments, the embodiment being for stimulation of nasal branches of the trigeminal nerve and, in said method embodiments, wherein the nasal branches of the trigeminal nerve are stimulated.

Embodiment 81.3 Any one of the preceding apparatus or method embodiments for topically directing air to, or in which air is topically to, the external ear, the embodiment being for the stimulation of any one or more of the following nerves in any combination (i) the auricular vagus nerve (auricular branch of the vagus nerve), (ii) the auriculotemporal nerve (a branch of the trigeminal nerve), and (iii) the great auricular nerve (formed by branches of spinal nerves C2 and C3), and in said method embodiments, wherein the one or more of said nerves is stimulated.

Embodiment 82. Any one of the preceding embodiments, for improving the performance of an attention-requiring task or activity by a/the user/subject. In one variation, the embodiment is used, performed or for operation during the performance of an attention-attention-requiring task or activity to improve the user's performance of the task or activity. The user may, for example, suffer from an attention deficit and/or may, for example, have ADD or ADHD.

Nasal branches of the trigeminal nerve and other nerves such as the olfactory nerves are bilaterally disposed on either side of the nasal septum, which maintains the separation of airstreams from the nostrils. Thus, the nasal breathing apparatus and method embodiments of the invention, including without limitation those providing asymmetric and/or alternating temperature airflow to the nostrils, may be used to stimulate and/or modulate the activity of these nerves, such as the trigeminal nerve via its nasal branches.

The external ear is supplied by three main nerves: (i) the auricular vagus nerve (auricular branch of the vagus nerve), (ii) the auriculotemporal nerve (a branch of the trigeminal nerve), and (iii) the great auricular nerve (formed by branches of spinal nerves C2 and C3). The spatial supply of these nerves to different parts of the external ear is described in Mercante et al., *Auricular Neuromodulation: The Emerging Concept beyond the Stimulation of Vagus and Trigeminal Nerves*, Medicines (Basel). 2018 March; 5(1):10, which is incorporated by reference herein in its entirety. The auricular branch of the vagus nerve mainly supplies the region consisting of the concha and the outer ear canal ("the vagus nerve region" or "VNR" of the external ear) and, at least in some cases, exclusively supplies the cymba conchae of the concha. The auriculotemporal nerve (a branch of the trigeminal nerve) mainly supplies the region consisting of the lateral anterior part of the external ear from the spine of helix to the crus of helix continuing over the tragus ("the auriculotemporal nerve region" or "ATNR" of the external ear). The remaining area of the lateral side of the external ear, which includes the rest of the helix and the anti-helix, and the area between the two, as well as anti-tragus and the lobule (collectively, "the great auricular nerve region" or "GANR" of the external ear) is mainly supplied by the great auricular nerve which is formed by branches of spinal nerves C2 and C3. Thus, airstreams, such as airstreams heated and/or cooled versus ambient temperature, may be directed on to one or more of these regions of the external ear to stimulate the corresponding auricular nerves. Accordingly, in embodiments of the invention in which air is topically directed onto a position/location of the external ear, the position/location may be in the VNR, ATNR or GANR. And, in embodiments of the invention in which air is topically directed onto different positions/locations of the external ear, which may be simultaneous and/or sequential application to the different positions, the different positions may be different positions within one or more of the VNR, ATNR and GANR and/or positions that are in different regions, i.e., in VNR and ATNR, in VNR and GANR, in ATNR and GANR, or in VNR and ATNR and GANR.

Breathing apparatus embodiments of the invention that include actuatable valves or actuatable manifolds under control of a controller to switch between different airstreams and/or airflow pathways, and generally between the different permitted states of particular such embodiments respectively, may be configured to provide one or more or all of the following modes of operation: a timed switching mode in which the switching occurs at timed intervals that may, for example, be uniform or varied (within a session of use), and which may be selectable or programmable with respect to time period(s) and occurrence of the switching to provide one or more routines; an alternate breathing cycle mode in which one or more provided sensors operably connected to the controller are configured to detect when expiration by the apparatus user is occurring or will occur and the controller is configured to perform the switching during (e.g., immediately after first detecting) each expiration or upon a preset or preselected number of expirations (such as upon every other expiration); and a user controlled mode in which a provided user input device, such as but not limited to a push button, is operably connected to the controller and the system is configured to perform the switching when the apparatus user or a person different than the user actuates/provides-input-to the user input device.

In any of the embodiments of the invention in which an airstream is actively provided, the provided airstream may have an at least substantially steady flow or an at least substantially pulsatile flow. Thus, for embodiments that include or involve an airflow generator or in which an airflow generator is provided, the airflow generator may be a steady airflow generator or a pulsatile airflow generator. Pulsatile airflow may, for example, be provided by disposing an actuatable on/off valve, such as a solenoid valve or 2-way solenoid-driven slider valve, which may be under control of a controller, in the flow path downstream of a steady airflow source, such as a steady airflow generator such as an electric fan or a pressurized air (or gas) tank with a regulator. Pulsatile airflow may, for example, be delivered with airflow pulses of 0.3-1.0 second duration and 0.3-1.0 second interval times between pulses.

It should be understood that wherever in the present disclosure the term comprising or the term including (or a term of similar scope) is recited in connection with the description of any embodiment or part or element thereof, a corresponding embodiment or part or element thereof reciting instead the term consisting essentially of or the term consisting of (or terms of similar scope) is also disclosed.

All publications, patents, patent applications and other documents cited in this application are hereby incorporated by reference in their entireties for all purposes.

Features described in connection with one embodiment disclosed herein may be used in conjunction with other embodiments disclosed herein, even if not explicitly exemplified in combination within. Further, while various specific embodiments have been illustrated and described in this disclosure, it will be appreciated that various changes can be made without departing from the spirit and scope of the invention.

What is claimed is:

1. A method for providing differential sensory stimulation to a human subject having a first nostril and a second nostril, comprising the steps of:
   over a course of multiple inhalations by the human subject, simultaneously,
      delivering air having a first temperature to the first nostril of the human subject for inhalation by the first nostril; and
      delivering air having a second temperature that is different than the first temperature to the second nostril of the human subject for inhalation by the second nostril,
   wherein the delivery of air having the first temperature and the delivery of air having the second temperature is switched between the first nostril and the second nostril of the human subject at least one time over said course of multiple inhalations.

2. The method of claim 1, wherein the delivery of air having the first temperature and the delivery of air having the second temperature is alternated between the first nostril and the second nostril of the human subject.

3. The method of claim 2, wherein the delivery of air having the first temperature and the delivery of air having the second temperature is alternated between the first nostril and the second nostril of the human subject for consecutive inhalations by the subject.

4. The method of claim 3, wherein
   the method is performed in an environment having an ambient temperature;
   the first temperature is below the ambient temperature; and
   the second temperature is above the ambient temperature.

5. The method of claim 4, wherein each of the first temperature and the second temperature differs from the ambient temperature by at least 5 degrees Celsius.

6. The method of claim 2, wherein
   the method is performed in an environment having an ambient temperature;

the first temperature is below the ambient temperature; and the second temperature is above the ambient temperature.

7. The method of claim 6, wherein each of the first temperature and the second temperature differs from the ambient temperature by at least 5 degrees Celsius.

8. The method of claim 1, wherein the delivery of air having the first temperature and the delivery of air having the second temperature is switched between the first nostril and the second nostril of the human subject at preselected time intervals.

9. The method of claim 8, wherein the method is performed in an environment having an ambient temperature;

the first temperature is below the ambient temperature; and the second temperature is above the ambient temperature.

10. The method of claim 1, wherein the method is performed in an environment having an ambient temperature;

the first temperature is below the ambient temperature; and the second temperature is above the ambient temperature.

11. The method of claim 10, wherein each of the first temperature and the second temperature differs from the ambient temperature by at least 5 degrees Celsius.

12. An apparatus for asymmetric temperature nostril breathing by a user having a first nostril and a second nostril, comprising:

a heated air providing element;

a cooled air providing element;

a valve for switching between a first state and a second state over a course of multiple inhalations by the user;

wherein the first state comprises simultaneously delivering heated air from the heated air providing element to the first nostril of the user and cooled air from the cooled air providing element to the second nostril of the user, and wherein the second state comprises simultaneously delivering heated air from the heated air providing element to the second nostril of the user and cooled air from the cooled air providing element to the first nostril of the user.

13. The apparatus of claim 12, further comprising a controller operably connected to the valve, said controller configured to (i) automatically actuate the valve, or (ii) actuate the valve in response to input by the user.

14. The apparatus of claim 13, further comprising at least one air flow generator configured to generate air flow.

15. The apparatus of claim 13, wherein the apparatus does not comprise an air flow generator.

16. The apparatus of claim 12, further comprising at least one air flow generator configured to generate air flow.

17. The apparatus of claim 12, wherein the apparatus does not comprise an air flow generator.

* * * * *